United States Patent
Ball

(10) Patent No.: US 7,160,326 B2
(45) Date of Patent: Jan. 9, 2007

(54) METHOD AND APPARATUS FOR IMPLANTATION OF SOFT TISSUE IMPLANT

(75) Inventor: Robert Ball, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 393 days.

(21) Appl. No.: 10/282,748

(22) Filed: Oct. 29, 2002

(65) Prior Publication Data

US 2004/0002723 A1   Jan. 1, 2004

Related U.S. Application Data

(60) Provisional application No. 60/392,152, filed on Jun. 27, 2002.

(51) Int. Cl.
*A61F 2/10* (2006.01)
*A61B 17/32* (2006.01)

(52) U.S. Cl. .................. 623/15.12; 623/23.72; 606/53; 606/132

(58) Field of Classification Search ............. 606/151, 606/131, 53, 54, 56, 60, 63, 72, 132; 292/256.6; 38/102.2; 600/201; 623/11.11, 15.12, 23.72
See application file for complete search history.

(56) References Cited

U.S. PATENT DOCUMENTS

| | | | |
|---|---|---|---|
| 2,127,903 A | | 8/1938 | Bowen |
| 3,562,820 A | | 2/1971 | Braun |
| 3,596,385 A | * | 8/1971 | Tachibana .................. 38/102.2 |
| 3,818,620 A | * | 6/1974 | Field et al. ................ 38/102.2 |
| 3,906,647 A | * | 9/1975 | Bates, Jr. .................. 38/102.2 |
| 4,422,250 A | * | 12/1983 | Golan ....................... 38/102.2 |
| 4,494,344 A | * | 1/1985 | Petcen ...................... 38/102.2 |
| 4,585,458 A | | 4/1986 | Kurland |
| 4,641,518 A | | 2/1987 | Hutchings |
| 4,644,639 A | * | 2/1987 | Atteberry et al. ........... 156/229 |
| 4,703,108 A | | 10/1987 | Silver et al. |
| 4,773,418 A | | 9/1988 | Hettich |
| 4,776,853 A | | 10/1988 | Klement et al. |
| 4,801,299 A | | 1/1989 | Brendel et al. |
| 4,902,508 A | | 2/1990 | Badylak et al. |
| 4,956,178 A | | 9/1990 | Badylak et al. |
| 5,269,788 A | * | 12/1993 | Nelson, III ................. 606/118 |
| 5,275,826 A | | 1/1994 | Badylak et al. |
| 5,281,422 A | | 1/1994 | Badylak et al. |
| 5,303,486 A | * | 4/1994 | Dell ......................... 38/102.2 |

(Continued)

FOREIGN PATENT DOCUMENTS

WO   WO 95/06439   3/1995

OTHER PUBLICATIONS

Johnson & Johnson Gateway internet presentation entitled "Restore Orthobiologic Implant"; Feb. 8, 2003; 3 pages.

(Continued)

*Primary Examiner*—Michael J. Hayes
*Assistant Examiner*—Michael G. Mendoza
(74) *Attorney, Agent, or Firm*—Barnes & Thornburg LLP

(57) ABSTRACT

A method of securing a soft tissue implant to damaged tissue of a patient is provided. The method includes preparing a layer of extracellular matrices (ECM) for surgery. The method further includes stretching the layer on a frame and securing the layer to the frame. The method includes placing a top surface of the layer adjacent the damaged tissue, drilling multiple holes generally simultaneously through the layer and tissue, and simultaneously inserting a fastener into each drilled hole.

9 Claims, 8 Drawing Sheets

U.S. PATENT DOCUMENTS

| | | |
|---|---|---|
| 5,352,463 A | 10/1994 | Badylak et al. |
| 5,372,821 A | 12/1994 | Badylak et al. |
| 5,503,638 A | 4/1996 | Cooper et al. |
| 5,554,389 A | 9/1996 | Badylak et al. |
| 5,555,653 A * | 9/1996 | Morgan .................... 38/102.2 |
| 5,722,191 A * | 3/1998 | Morgan .................... 38/102.2 |
| 5,788,625 A | 8/1998 | Plouhar et al. |
| 6,099,567 A | 8/2000 | Badylak et al. |
| 6,154,991 A * | 12/2000 | Duncan et al. ............ 38/102.2 |
| 6,171,344 B1 | 1/2001 | Atala |
| 2002/0087214 A1 * | 7/2002 | Kropp et al. ............ 623/23.71 |

OTHER PUBLICATIONS

Cook® Online product information presented by Cook Biotech, Inc. entitled "Oasis™ Wound Dressing"; Jan. 21, 2003; 2 pages.

Cook® Online product information presented by Cook Biotech, Inc. entitled "Surgisis™ Soft-Tissue Graft"; Jan. 21, 2003; 2 pages.

\* cited by examiner

METHOD AND APPARATUS FOR IMPLANTATION OF SOFT TISSUE IMPLANT

CROSS-REFERENCE TO RELATED APPLICATIONS

This application claims priority under 35 U.S.C. 119(e) to U.S. Provisional Application Ser. No. 60/392,152, filed Jun. 27, 2002, which is expressly incorporated by reference herein.

FIELD OF INVENTION

The present invention relates generally to devices for attaching, repairing, or regenerating damaged or diseased cartilage.

BACKGROUND

It is known to use naturally occurring extracelluar matrices (ECMs) or any soft tissue implant to provide a scaffold for tissue repair and regeneration. One such ECM is small intestine submucosa (SIS). SIS has been described as a natural acellular biomaterial used to repair, support, and stabilize a wide variety of anatomical defects and traumatic injuries. See, for example, Cook® Online New Release provided by Cook Biotech Inc. at "www.cookgroup.com". The SIS material is derived from porcine small intestinal submucosa that models the qualities of its host when implanted in human soft tissues. Further, it is taught that the SIS material provides a natural scaffold-like matrix with a three-dimensional structure and biochemical composition that attracts host cells and supports tissue remodeling. SIS products, such as OASIS and SURGISIS, are commercially available from Cook Biotech Inc., Bloomington, Ind.

Another SIS product, RESTORE Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, and it is a naturally occurring ECM composed of more than 90 percent collagen that has been cleaned, processed, and sterilized. During seven years of preclinical testing in animals, there were no incidences of infection transmission from the implant to the host, and the RESTORE Implant has not decreased the systemic activity of the immune system.

While small intestine submucosa is available, other sources of submucosa are known to be effective for tissue remodeling. These sources include, but are not limited to, stomach, bladder, alimentary, respiratory, or genital submucosa, or liver basement membrane. See, e.g., U.S. Pat. Nos. 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, other collagen matrices are known, such as lamina propria and stratum compactum, for example.

Also, while reference is made to SIS, it is understood that other naturally occurring ECMs or any soft tissue implant such as skin or other laminar pliable structures, for example are within the scope of this invention.

The RESTORE patch and other similar ECM devices are inherently flexible which allows the devices to move, fold, and twist during placement and attachment of the device during surgery, for example.

SUMMARY

According to the present disclosure, a method and apparatus for securing a soft tissue implant to damaged tissue of a patient is provided. The method includes preparing a layer of extracellular matrices (ECM) or other such materials for surgery. The method further includes stretching the layer on a frame and securing the layer to the frame. The method includes placing a top surface of the layer adjacent the damaged tissue, drilling multiple holes generally simultaneously through the layer and tissue, and generally simultaneously inserting a fastener into each drilled hole.

A device is provided for securing and tensioning the soft tissue implant thereon prior to securing the soft tissue implant to damaged tissue. The device includes a frame and a means for securing the implant to the frame. In one illustrative embodiment, the frame includes an inner frame member having an outer surface, and an outer frame member to be positioned about the inner frame member to capture the soft tissue implant about the outer surface. In another illustrative embodiment, the frame includes a frame member having holes formed therein and the securing means includes fasteners inserted through the implant into the holes. In yet another illustrative embodiment, the securing means is an adhesive.

BRIEF DESCRIPTION OF THE DRAWINGS

FIG. 3 is a sectional view of the SIS patch and the inner ring showing the SIS patch to be draped over the inner ring.

FIG. 4 is a sectional view similar to FIG. 3 showing the SIS patch draped over the inner ring.

FIG. 5 is a sectional view similar to FIGS. 3 and 4 showing the outer ring of the hoop placed over the SIS patch and around the inner ring of the hoop to position a perimeter of the SIS patch between the outer ring and inner ring to secure and tension the SIS patch within the hoop.

FIG. 9 is a sectional view showing the tensioned SIS patch secured to the hoop and placed patch-side-down over damaged tissue of the patient, and also showing the drill head positioned over the SIS patch in preparation for puncturing holes through the SIS patch and tissue of the patent.

FIG. 10 is a sectional view of the tensioned SIS patch secured to the hoop and positioned patch-side-down after the drill head has punctured holes through the SIS patch and the tissue of the patient showing a device for fastening the patch to the tissue by inserting rivets through the holes drilled by the drill head.

FIG. 11 is a perspective view showing the SIS patch secured to the patient's tissue by the rivets inserted by the device shown in FIG. 10.

FIG. 12 is a perspective view similar to FIG. 11 showing the SIS patch secured to the patient's tissue after the outer ring of the hoop has been removed.

FIG. 13 is a perspective view similar to FIGS. 11 and 12 showing the SIS patch secured to the patient's tissue after the inner ring of the hoop has been removed.

DETAILED DESCRIPTION OF THE DRAWINGS

Figure 1:
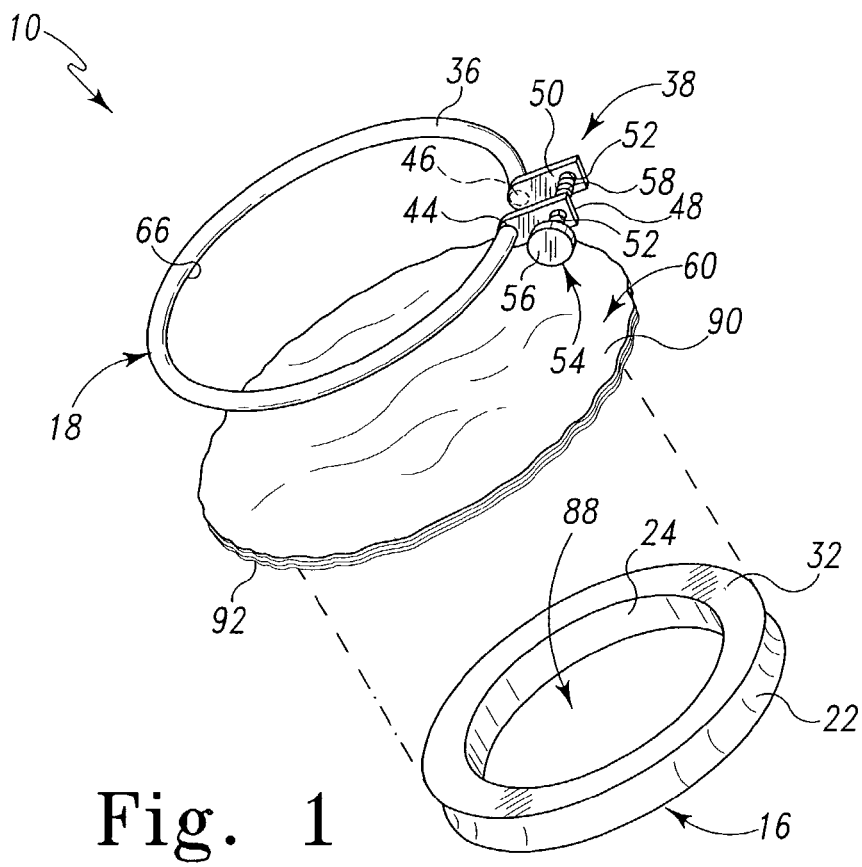
FIG. 1 is an exploded perspective view of a tensioning hoop or frame of the present disclosure showing an inner ring of the hoop including a curved outer wall and an outer ring of the hoop to be placed around the inner ring and tightened about the inner ring by a thumb screw, and further showing a multi-layered patch of SIS to be tensioned between the inner and outer rings of the hoop.
Figure 2:
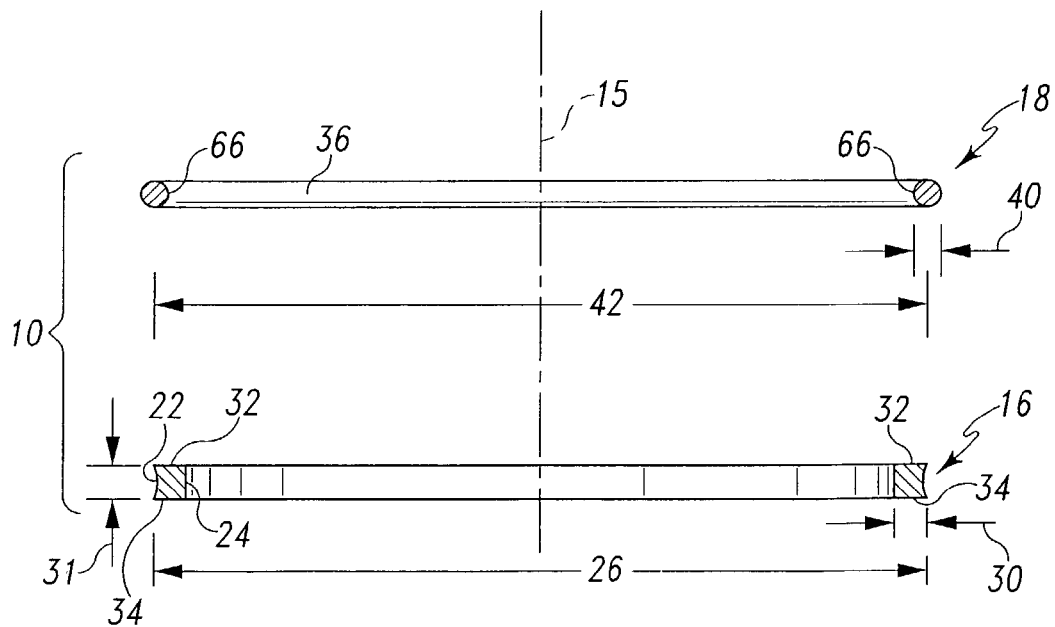
FIG. 2 is a sectional view of the outer and inner rings of the hoop.

A method and apparatus for implanting a pliable, soft tissue implant 60 is provided. As shown in FIGS. 1 and 2, a tensioning hoop or frame 10 is provided for tensioning and holding the implant 60 during surgery. Hoop 10 supports the implant 60 and allows a caregiver to provide appropriate tension loads onto the implant 60 prior to placement of the implant 60 during surgery. Further, by supporting the implant 60 on hoop 10, positioning and attachment of the implant 60 onto damaged tissue 68 shown in FIGS. 9–13, for example, may be made easier and less time consuming. The illustrative tissue implant 60 may be, for example, a RESTORE Implant from DePuy Orthopaedics, Inc. or an implant similar to the RESTORE Implant. Illustratively, the implant 60 may be a plurality of layers of ECM material, or other soft tissue material, laminated together to provide a patch of implant material. Further illustratively, the implant material may be pliable.

Figure 7:
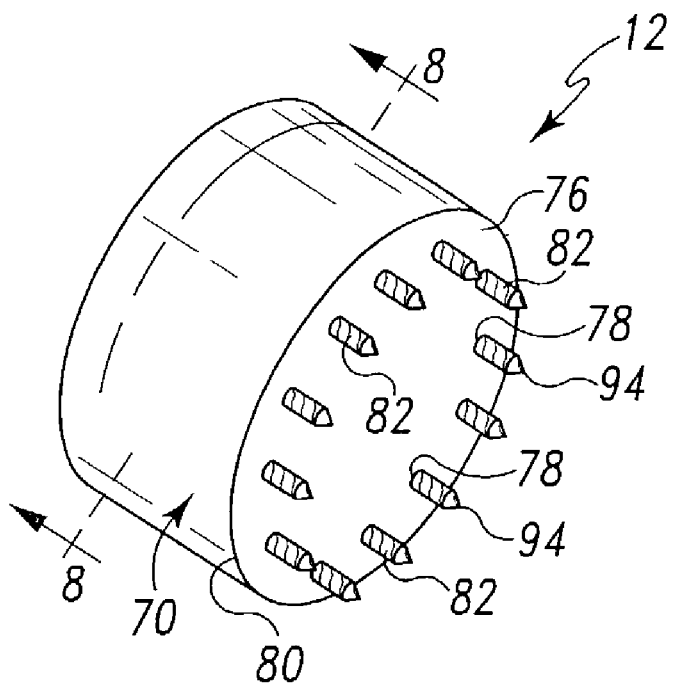
FIG. 7 is a perspective view of a drill head of the present disclosure showing bits of the drill head for puncturing holes through the SIS patch and into tissue of a patient in preparation for securing the SIS patch to the prepared tissue of the patient.
Figure 8:
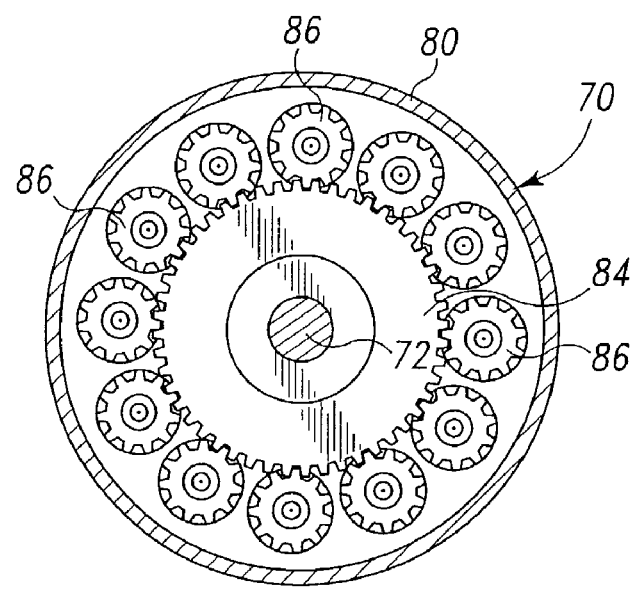
FIG. 8 is a sectional view through line 8—8 of FIG. 7 showing a central drive gear of the drill head and multiple peripheral or passive gears around the central drive gear and in communication with the central drive gear for rotational movement with the central drive gear in a direction opposite the central drive gear to rotate and advance the bit coupled to each peripheral gear.
Figure 9:
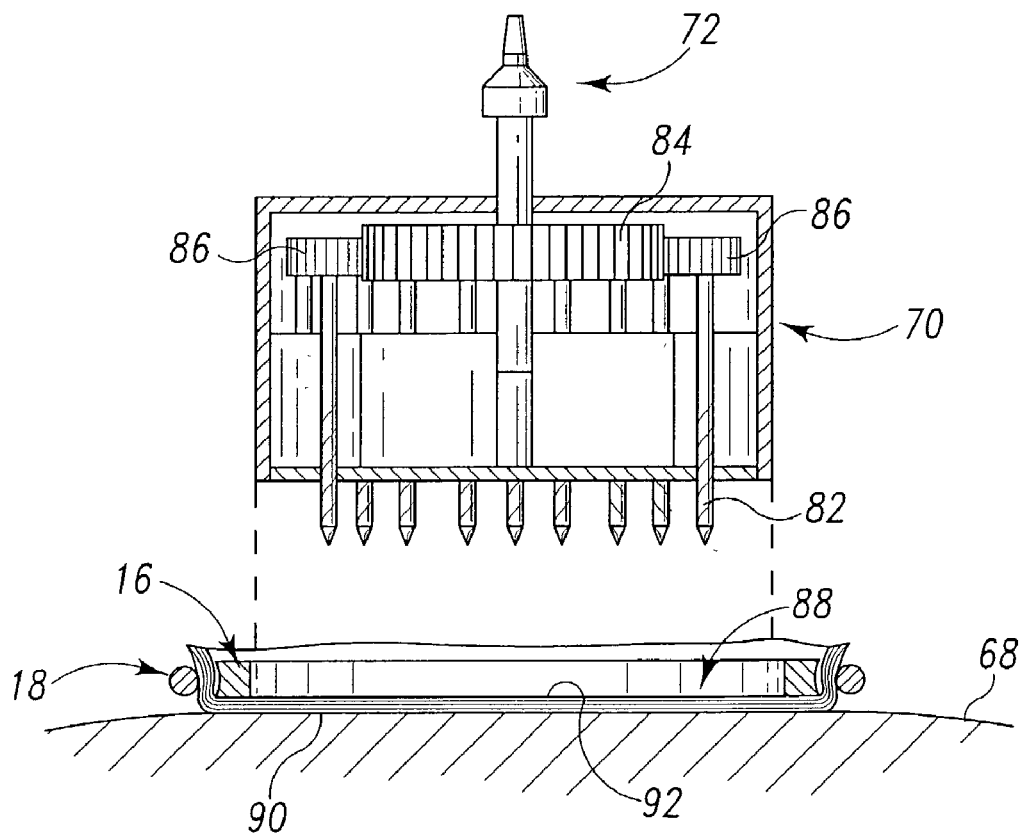
FIGS. 9–13 illustrate steps for preparing and securing the SIS patch to the patient's damaged tissue.
Figure 10:
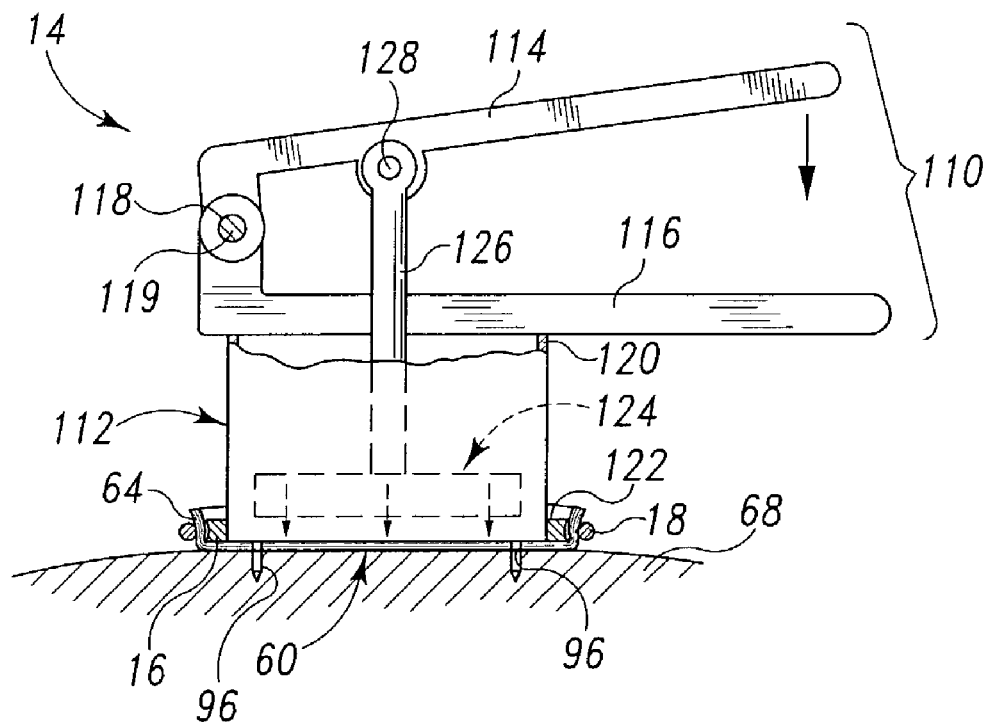

As shown in FIGS. 7–9, a drill head 12 is provided to prepare the implant 60 for attachment to the damaged tissue 68 during surgery. Drill head 12 punctures the implant 60 and the damaged tissue 68 in multiple areas. A device 14, is also provided, as shown in FIG. 10, for inserting rivets or other fasteners, for example, into puncture holes 96 made by drill head 12 to secure the implant 60 to the damaged tissue 68.

Looking now to FIG. 1, hoop 10 includes an inner ring or frame member 16 and an outer ring or frame member 18. As shown in FIGS. 1 and 2, inner member 16 is generally circular in shape and includes an outer diameter (OD) surface 22 which is concave in cross-section as illustrated in FIG. 2. Inner member 16 further includes an internal diameter (ID) surface 24 which is generally cylindrical about an axis 15 of the hoop 10. As shown in FIG. 2, inner surface 24 is generally vertical when viewed in cross-section. Illustratively, inner member 16 has a diameter 26 of 60.0 mm measured from an outer edge of outer diameter surface 22. Further illustratively, inner member 16 has a thickness 30 and a height 31 of 12.5 mm and outer surface 22 has a radius of 8.0 mm. Inner member 16 further includes a top surface 32 and a bottom surface 34.

Outer member 18, as shown in FIG. 1, is also generally circular in shape and includes a ring member 36 and a tightener 38 coupled to ring member 36. Ring member 36 has a circular cross-section, as shown in FIG. 2, illustratively having a diameter 40 of 8.0 mm. Further illustratively, outer member 18 normally has a diameter 42 of 60.0 mm measured from a center point of each cross-section.

Although inner and outer members 16, 18 have been described as having the above-defined dimensions, it is within the scope of this disclosure to include an inner member and an outer member having other suitable dimensions. Further, it is within the scope of this disclosure for inner member 16 and outer member 18 to take the form of any suitable shape such as a rectangle, square, oval, triangle, etc. For example, an elongated shape may be desired to put tension on the implant 60 in mainly one direction. The inner and outer members 16, 18, therefore, are inner and outer members of a tensioning frame which may be in the form of any suitable shape.

Figure 17:
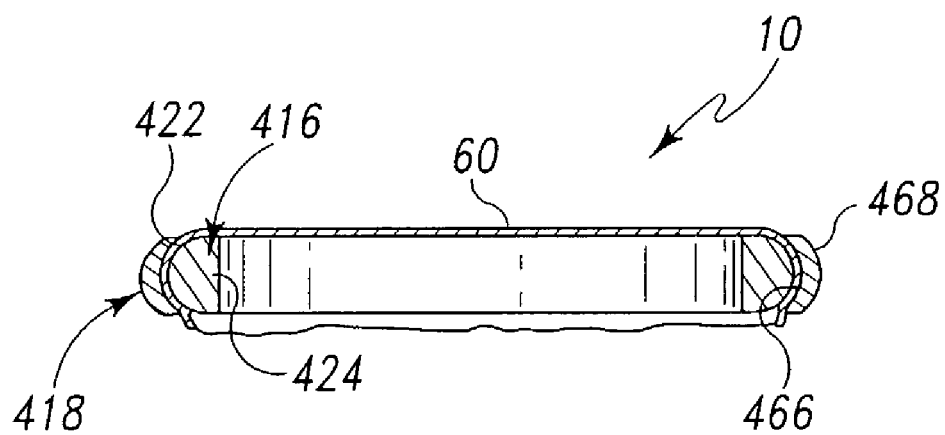
FIG. 17 is a sectional view of still another alternative tensioning frame, similar to the frame shown in FIG. 1, showing the SIS patch secured between inner and outer members of the frame.

Further, for example, an alternative tensioning hoop or frame 410 may be provided such as that shown in FIG. 17. Frame 410 is similar to frame 10 and includes an inner member 416 and an outer member 418. Unlike frame 10, however, an outer surface 422 of the inner member 416 is convex when viewed in cross-section and an inner surface 466 of the outer member 418 is concave when viewed in cross-section. Therefore, as shown in FIG. 17, outer member 418 cups and surrounds outer surface 422 of inner member 416. Implant 60 is tensioned over inner member 416 and secured to frame 410 between inner member 416 and outer member 418. Inner member 416 further includes an inner surface 424 and outer member 418 further includes an outer surface 468.

As mentioned above with respect to frame 10, outer member 18 is provided to secure and tension the implant on inner member 16. It is within the scope of this disclosure to include any suitable type of securing means to secure the implant 60 to the inner member 16. For example, the outer member may be a rubber-band-like structure to be stretched around inner member 16 and the implant 60 to secure the implant 60 to the inner member 16. Alternatively, the outer member may be a ropelike structure, for example, tied around inner member 16 and the implant 60. In other words, the outer member may be any suitable structure placed around inner member 16 and the implant 60 so that the implant 60 is secured to and tensioned on inner member 16.

Further, it is within the scope of this disclosure to include a tensioning frame having only a single-member frame over which the implant 60 is tensioned and secured. For example, the single frame member may be any suitable shape, as discussed above, and the implant 60 may be secured to the single frame member in a manner other than through the use of an outer frame member tightened around the inner frame member and implant, as is described below.

Figure 14:
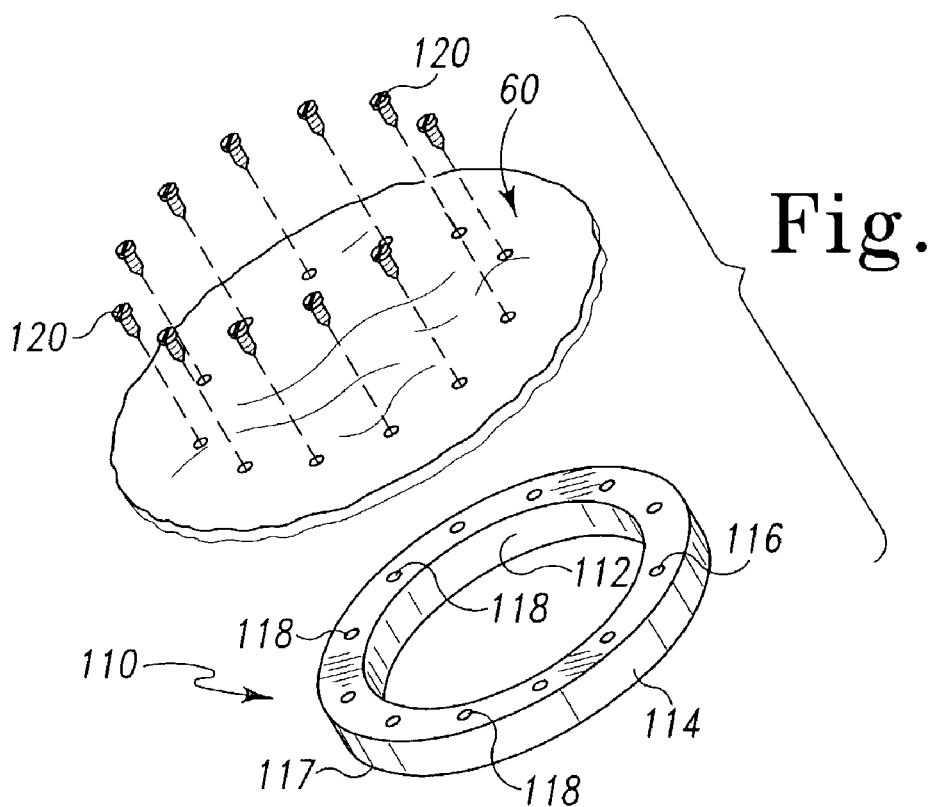
FIG. 14 is a perspective view of an alternative tensioning hoop or frame showing a single-member frame including holes for receiving rivets or the like to secure the SIS patch to the frame after the SIS patch has been placed on and tensioned over the frame.

For example, as shown in FIG. 14, an alternative frame 110 is provided for securing and tensioning soft tissue implant 60 thereon. Frame 110 is a single-member frame and is illustratively circular. Frame 110 includes an inner surface 112, an outer surface 114, a top surface 116, and a bottom surface 117. Further, frame 110 includes holes 118 drilled through top surface 116, as shown in FIG. 14. It is within the scope of the disclosure for holes 118 to extend partially or fully through frame 110. The implant 60 is secured to frame 110 by fasteners 120 pushed through implant 60 and into holes 118 so that the implant 60 is adjacent to top surface 116 of frame 110. The securing or fastening means of the implant 60 to the frame 110 may also be accomplished through the use of sutures, pins, rivets, staples, etc. sewn through or pushed through the implant 60 and holes 118 of frame 110. Further, it is within the scope of this disclosure for frame 110 to not include holes 118 for receiving fastners 120 therethrough. For example, fasteners 120 (or rivets, pins, staples, or the like) may be pushed through the implant 60 and into frame 110. It is further within the scope of the disclosure for frame 110 to be any suitable shape for tensioning and securing the implant 60 thereon such as an oval, square, triangle, etc., for example.

Figure 15:
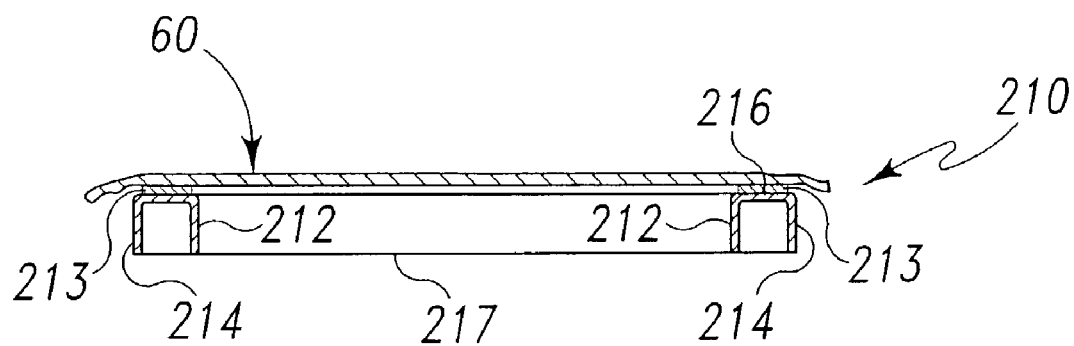
FIG. 15 is a sectional view of another alternative tensioning frame of the present disclosure showing a single-member frame including adhesive on a top surface of the frame to secure and tension the SIS patch thereon.

In another illustrative embodiment, shown in FIG. 15, a single-member frame 210 is provided to which the implant 60 may be permanently or temporarily bonded through the use of a glue or adhesive 213. Frame 210, similar to frame 110, includes an inner surface 212, an outer surface 214, a top surface 216, and a bottom surface 217. Adhesive 213 is attached to top surface 216 and implant 60 is tensioned and stretched over frame 210 and is adhered to frame 210 by adhesive 212. Adhesive 212 may be any suitable type of adhesive for use with soft tissue implants. At any rate, it is within the scope of this disclosure to secure the implant to any frame, including single or multi-member frames, as discussed above. It is appreciated that frame 210 having adhesive 213 may be any suitable shape such as an oval, triangle, square, rectangle, etc., having a surface to carry the adhesive 213 thereon so that implant 60 may be tensioned and secured to the frame by the adhesive.

Figure 16:
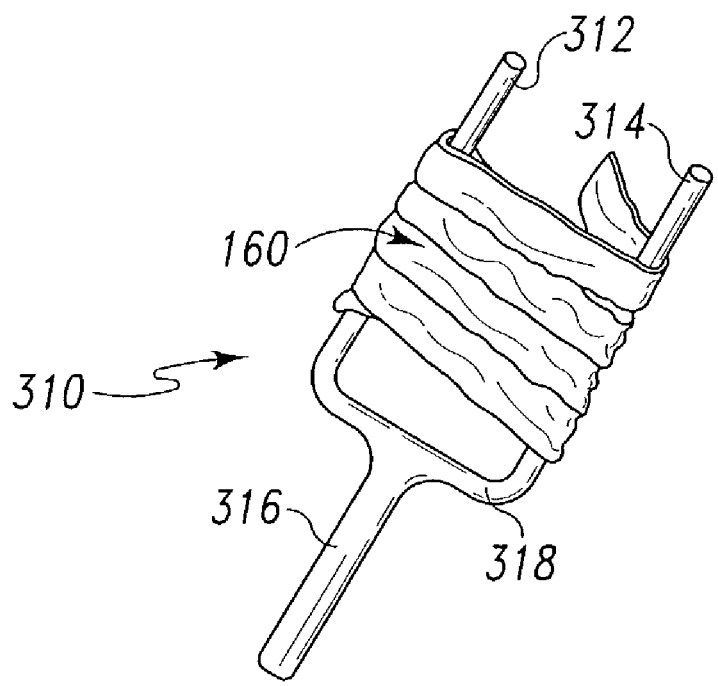
FIG. 16 is a perspective view of yet another alternative tensioning frame showing a single-member "Y-shaped" frame having two arms and further showing a long strip of SIS wrapped about the two arms to tension and secure the SIS strip to the frame.

Further illustratively, an SIS implant, such as implant 160, may be wrapped around and secured or fastened to a frame. For example, an illustrative "Y-shaped" frame 310 is shown in FIG. 16. Frame 310 includes a first arm 312 and a second arm 314 spaced-apart from first arm 312. Frame 310 further includes a handle 316 coupled to each of the first and second arms 312, 314 through a generally horizontal member 318. The implant 160, which is illustratively a strip of SIS or other soft tissue, is wrapped around and secured to the first and second arms 312, 314 of the frame 310 so that the implant 160 is more manageable prior to surgery, for example. Implant 160 may also be tensioned as it is wrapped around the first and second arms 312, 314 of frame 310.

Although implant 160 is shown, it is within the scope of this disclosure for frame 310 to be used with other types of implants having other suitable shapes which may be wrapped and tensioned around arms 312, 314 of frame 310. The implant 160 may be secured to one or both of arms 312, 314 by any suitable means such as that discussed above including the use of a pin, suture, rivet, staple, adhesive, etc. Further, although illustrative frame 310 is generally Y-shaped, it is within the scope of this disclosure to include a frame used for wrapping an implant therearound having any other suitable shape such as those discussed above, for example, including a rectangle, square, oval, or circle, for example.

It is also within the scope of this disclosure for the outer and/or inner surfaces of the frames 10, 110, 210, 310, 410 discussed above to be textured for gripping the implant 60 once implant 60 is placed thereon. Furthermore, it is within the scope of this disclosure for each of the frames, 10, 110, 210, 310, 410 discussed above to include spikes coupled to the outer and/or inner surfaces of the respective frames so that the implant 60 may be pierced by the spikes and gripped by the spikes to secure the implant 60 to the frame.

Referring now to tensioning hoop 10, shown in FIGS. 1–5, tightener 38 is provided for tightening the outer member 18 and decreasing diameter 42 of ring member 36. As shown in FIG. 1, ring member 36 includes a first end 44 and a second end 46 normally spaced-apart from first end 44. A first flange 48 of tightener 38 is coupled to first end 44 and a second flange 50 of tightener 38 is coupled to second end 46. Each flange 46, 48 includes a threaded aperture 52 for receiving a thumb screw 54. Thumb screw 54 includes a head 56 and a threaded body 56 received through each aperture 52. As head 56 of thumb screw 54 is turned clockwise, first and second flanges 48, 50 are drawn closer together to reduce the normal diameter 42 of outer member 18.

Hoop 10 is assembled by placing outer member 18 about inner member 16 so that ring member 36 engages and is received within the outer surface 22 of inner member 16. Curved outer surface 22 generally prevents outer member 18 from slipping or detaching from inner member 16. Outer member 18 may then be tightened about inner member 16, as desired, by rotating thumb screw 54 in a clockwise direction. Conversely, rotating thumb screw 54 in a counterclockwise direction moves first and second flanges 48, 50 apart from each other to loosen outer member 18 around inner member 16 so that outer member 18 may be separated from inner member 16 to disassemble hoop 10.

As mentioned above, hoop 10 is provided to secure and tension a piece of soft tissue implant 60 in preparation for surgery. Illustrative implant 60 is a RESTORE™ SIS patch 60, as shown in FIGS. 1 and 3–5, and is the illustrative soft tissue implant provided for use with the hoop 10. It is within the scope of this disclosure, however, for hoop 10 and all illustrative alternative frames 110, 210, 310, 410 to be used to secure any suitable soft tissue implant including any suitable ECM implant or SIS implant. Patch 60 is generally circular in shape and illustratively comprises ten layers of SIS material oriented in various directions. Illustratively, patch 60 has a diameter 62 (shown in FIG. 3) of 100.0 mm.

Figure 3:
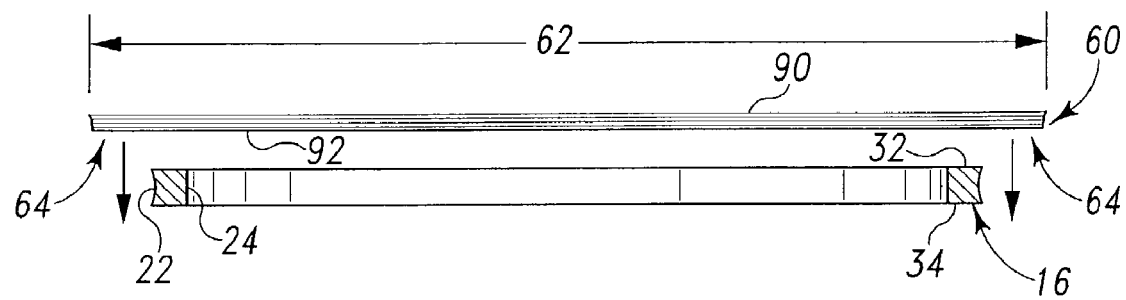
FIGS. 3–5 illustrate the steps for securing the SIS patch within the hoop.
Figure 4:
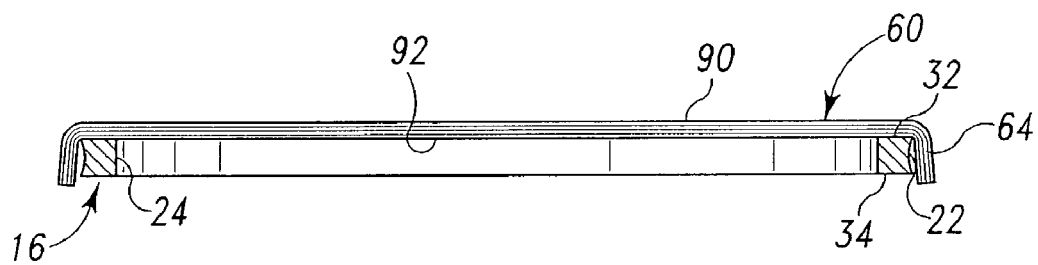
Figure 5:
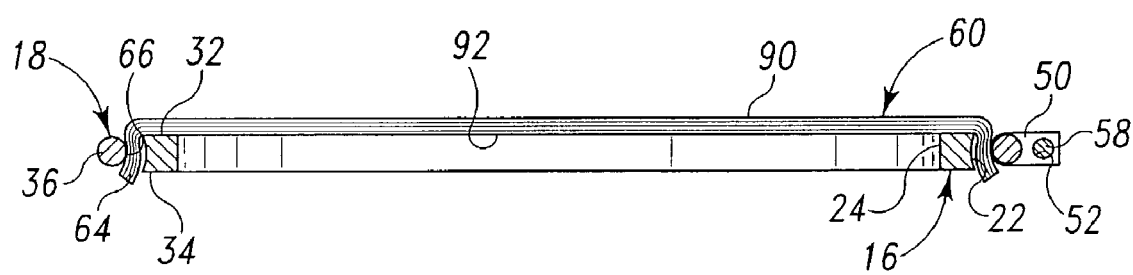
Figure 6:
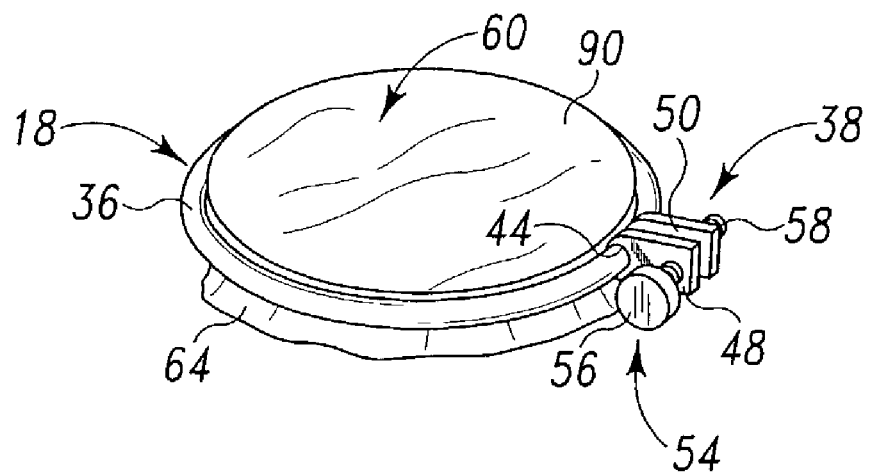
FIG. 6 is a perspective view of the SIS patch stretched and secured within the rings of the hoop showing the thumb screw of the outer ring having been rotated clockwise to tighten the outer ring on the inner ring to further tension the SIS patch across the inner hoop and to place stresses on the SIS patch prior to implantation.

To secure patch 60 to hoop 10 in preparation for surgery, a caregiver places patch 60 over inner member 16, as shown in FIGS. 3–5. Patch 60 is flexible in nature and is also larger than inner member 16 so that an outer peripheral portion 64 of patch 60 hangs outside of inner member 16, as shown in FIG. 5. Once patch 60 is properly positioned over inner member 16, outer member 18 is placed over and around inner member 16 and peripheral portion 64 of patch 60 to rest within and adjacent surface 22 of inner member 16. As shown in FIG. 6, peripheral portion 64 of patch 60 is secured between outer surface 22 of inner member 16 and an inner surface 66 of outer member 18.

Once outer member 18 is placed within curved surface 22 of inner member 16, the caregiver may tighten thumb screw 54 to tighten ring member 36 about inner member 16 and place tension on patch 60. As desired, the caregiver is able to stretch the patch 60 across the inner member 16 to put appropriate tension loads into patch 60 prior to the placement of patch 60 on the surgery site. By stretching patch 60 taut over inner member 16, patch 60 is strained radially with respect to the inner member 16. The normally loose patch 16 becomes a manageable, taut sheet, as shown in FIG. 6, that can be precisely manipulated for positioning during surgery.

Inner member 16 and outer member 18 of hoop 10 may each be made from a plastic, metal or other suitable material. The inner and outer members 16, 18 may also be flexible and bendable for ease of use and manipulation of the implant during surgery. Further, as mentioned above, the inner and outer surfaces of the inner and outer members 16, 18 may be textured or include ridges to grip the implant 60 and reduce possible slippage between the implant and hoop 10.

Figure 11:
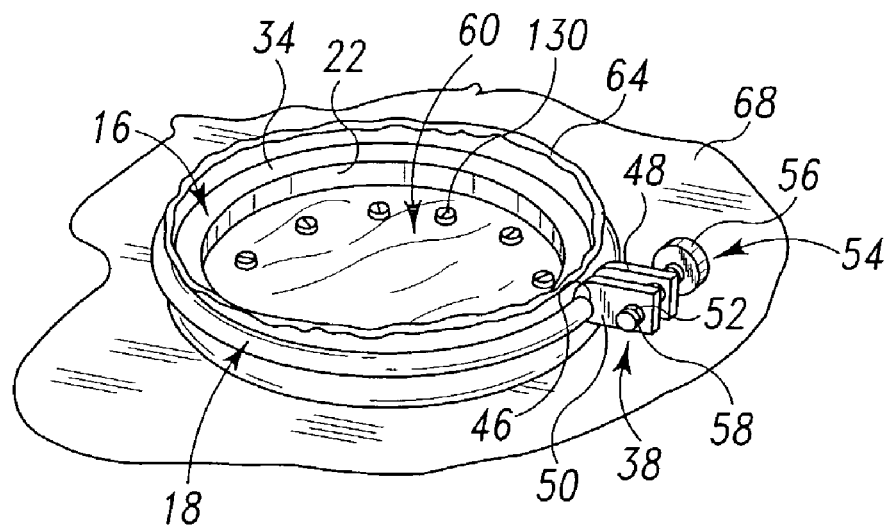
Figure 12:
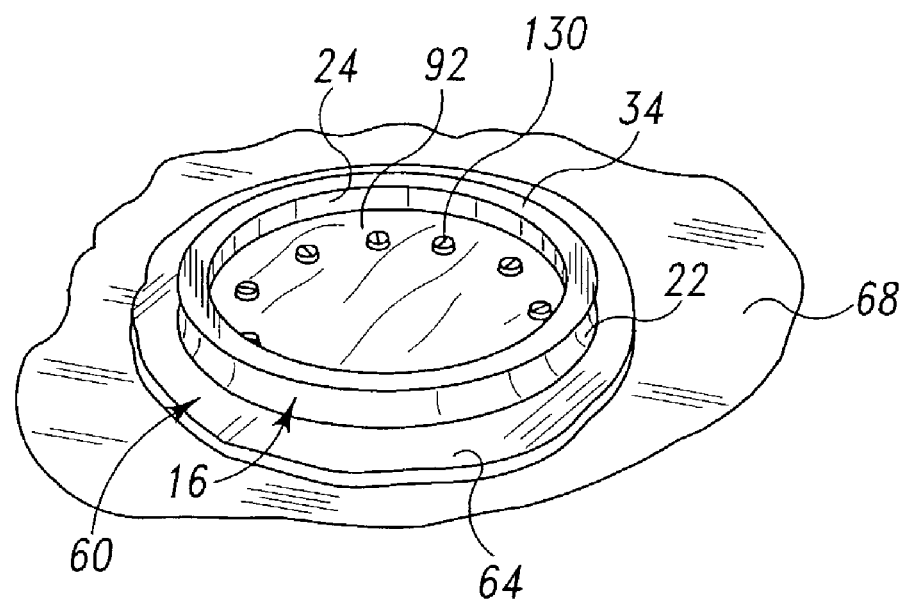

As mentioned above, the present method of implanting a soft tissue implant, illustratively patch 60, further includes the use of drill head 12 and device 14 for preparing and securing the patch 60 to damaged tissue 68, as shown in FIGS. 9–11. Looking now to FIGS. 7 and 8, drill head 12 includes a cylindrical hub 70 coupled by a connector 72, (shown in FIG. 9) illustratively, a "Hudson" connector, to a power drill (not shown). Hub 70 includes a flat end 76 including a ring of apertures 78 formed therein and positioned near an outer edge 80 of end 76. Flat end 76 of hub 70 is sized to fit within an aperture 88 of inner ring 16. Hub 70 further includes pins or drill bits 82 for puncturing patch 60 and damaged tissue 68, as discussed in more detail below.

As shown in FIG. 8, hub 70 includes a central drive gear 84 coupled to the connector 72 to connect with the power drill. Surrounding drive gear 84 are smaller peripheral gears 86 each in engagement with central drive gear 84 for rotational movement by gear 84. Each of the peripheral gears 86 rotates in a direction opposite that of the central gear 84. For example, if the central gear 84 rotates in a clockwise direction, each peripheral gear 86 is urged to rotate in a counterclockwise direction. One bit 82 is coupled to each peripheral gear 86 so that when power is supplied to drive gear 84 through the power drill, the rotation of drive gear 84 will cause simultaneous rotation of each peripheral gear 86 (in a direction opposite that of the drive gear) and each bit 82 coupled to each peripheral gear 86. Illustratively, each bit 82 includes threads 83 so that the rotating bits 82, when forced into patch 60 and tissue 68, drill holes 96.

Alternatively, each bit 82 may also be advanced through the respective aperture 78 as gears 86 rotate. It is within the scope of this disclosure for each bit 82 to be reciprocated through the use of a cam (not shown). It is also within the scope of this disclosure for bits 82 to be threaded or reverse-threaded. For example, the bits 82 rotate in the opposite direction of the drive gear 84. Therefore, a reverse-threaded bit may be appropriate for use when the drive gear 84 is operated to rotate in a standard clock-wise direction. Conversely, if the power drill is set to operate in a reverse-mode, and the drive gear 84 is rotated in a counter-clockwise direction, a threaded bit may be appropriate for the bit's clockwise rotation. As mentioned above, illustrative bits 82, shown in FIG. 7, are threaded. However, it is within the scope of this disclosure to include bits that are not threaded such as pins, or the like.

To prepare patch 60 for attachment to tissue 68, a contact surface 90 of patch 60 (see FIG. 9) is placed adjacent tissue 68 while held within hoop 10, as shown in FIG. 10. For example, the RESTORE patch 60 may be placed over a weak deltoid muscle shown as tissue 68. However, it is within the scope of the present invention to use patch 60, or another soft tissue implant, and hoop 10 with any type of damaged or weak tissue in need of repair. In any event, the patch 60 and hoop 10 combination is placed patch-side-down adjacent tissue 68. Drill head 12 is placed within hoop 10 so that end 76 of hub 70 is near or adjacent an opposite surface 92 of patch 60. As mentioned before, flat end 76 of hub 70 is sized to fit within aperture 88 of inner ring 16. Drill head 12 is activated by the power drill to rotate and advance pins 82 toward patch 60. A tip 94 of each pin 82 punctures through patch 60 and into damaged tissue 68 generally simultaneously to create multiple holes 96, as shown in FIG. 10, through patch 60 and into tissue 68.

Once the holes 96 have been created through patch 60 and into tissue 68, device 14 is used to secure patch 60 to tissue 68. As shown in FIG. 10, device 14 includes a handle 110 and an outer cylinder 112 coupled to handle 110. Handle 110 includes first and second hinged members 114, 116 coupled to each other at pivot point 118 by a pin 119. Cylinder 112 is a hollow wall coupled at a top end 120 to second member 116 and open at a bottom end 122 for communication with opposite surface 92 of patch 60. Cylinder 112 is generally sized to fit within aperture 88 of inner ring 16, as shown in FIG. 10.

Device 14 further includes a head 124 and a rod 126 coupled to the head 124 at one end and coupled to first member 114 at another end by a pin 128. Head 124 houses and/or carries fasteners 130 such as anchors, rivets, nails, tacks, screws, or the like for securing patch 60 to tissue 68. The fasteners 130 may be made for insertion through tissue, such as patch 60 and damaged tissue 68, only or for insertion through tissue and bone. Fasteners 130 may be made of metal or plastic, or another material suitable for securing patch 60 to tissue 68. Further, fasteners 30 may be bioabsorbable or non-bioabsorbable. For example, bioabsorbable fasteners 130 may be made of SIS or another ECM.

In operation, a user places cylinder 112 within aperture 88 of inner ring 16. After aligning the holes 96 drilled through the patch 60 by drill head 12 with the fasteners 130 carried on head 124, the user grasps handle 110 and moves member 114 in a generally downward direction, as shown in FIG. 10, so that member 114 pivots relative to member 116 about pivot point 118. Rod 126 and head 124 are therefore also moved in a downward direction within cylinder 112 as rod 126 pivots about pin 128 to remain in a generally vertical position. As head 124 is moved toward patch 60, fasteners 130 are inserted within the holes 96 created by drill head 12.

Figure 13:
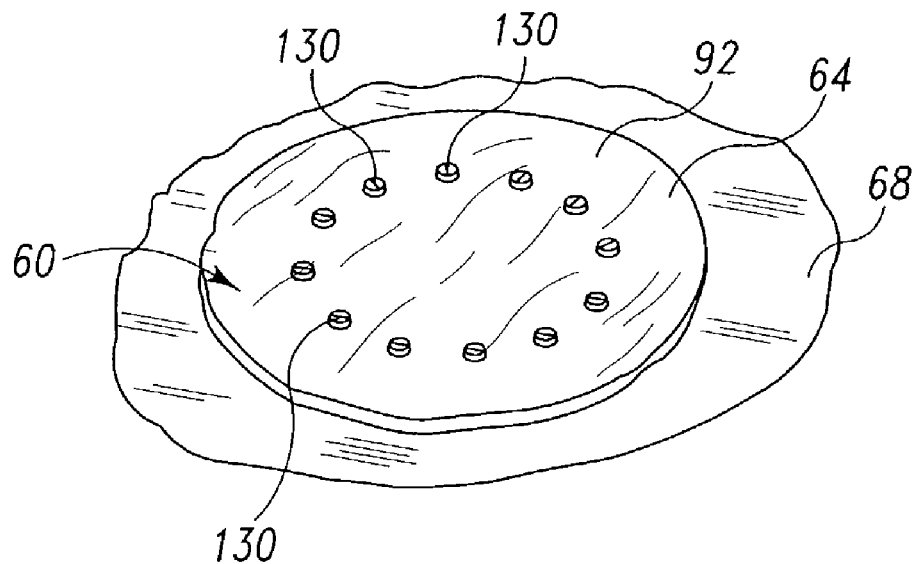

Once all the fasteners 130 have been inserted, patch 60 is securely coupled to tissue 68 and device 14 is removed, as shown in FIG. 11. To remove hoop 10, the caregiver loosens the outer ring 18 by rotating thumb screw 54 in a counter-clockwise direction. Outer ring 18 is then removed from inner ring 16 in a direction away from tissue 68 to release the outer peripheral portion 64 of patch 60 from between inner ring 16 and outer ring 18. Inner ring 18 is subsequently removed from patch 60, as shown in FIG. 13, to leave patch 60 tensioned and secured to tissue 68 by fasteners 130. If desired, the caregiver may trim patch 60 by cutting off the outer peripheral portion 64, or the extra material outside fasteners 130, of patch 60.

Although this invention has been described in detail with reference to certain embodiments, variations and modifications exist within the scope and spirit of the invention as described and defined in the following claims.

The invention claimed is:

1. An orthopaedic device comprising:
   a soft tissue implant,
   an inner frame having a concave outer surface, and
   an outer frame to be positioned about the inner frame to capture the soft tissue implant about the outer surface, wherein said device is sterile, and
   wherein the outer frame includes a member having a first end and a second end normally spaced apart from the first end, and an apparatus configured to tighten and loosen the outer frame about the inner frame, the apparatus including a flange coupled to each of the first and second ends and a screw at least partially received within an aperture of each of the flanges.

2. The device of claim 1, wherein the inner frame is generally circular.

3. The device of claim 1, wherein the inner frame has a diameter of approximately 60 millimeters.

4. The device of claim 1, wherein the member has a circular cross-section.

5. The device of claim 4, wherein the member has a diameter of 60 millimeters measured from the center of a cross-section.

6. The device of claim 4, wherein the circular cross-section has a diameter of eight millimeters.

7. The device of claim 1, wherein the inner frame and the outer frame are made of a flexible material.

8. The device of claim 1, wherein the outer surface of the inner frame is textured.

9. The device of claim 8, wherein a portion of the outer frame is textured.

* * * * *